United States Patent
Axén et al.

(10) Patent No.: US 10,611,646 B2
(45) Date of Patent: Apr. 7, 2020

(54) METHOD FOR PRODUCING CALCIUM SULPHATE HEMIHYDRATE WITH UNIQUE PROPERTIES

(71) Applicant: LIDDS AB, Uppsala (SE)

(72) Inventors: Niklas Axén, Järlåsa (SE); Stefan Gruden, Uppsala (SE)

(73) Assignee: LIDDS AB, Uppsala (SE)

(*) Notice: Subject to any disclaimer, the term of this patent is extended or adjusted under 35 U.S.C. 154(b) by 0 days.

(21) Appl. No.: 16/431,926

(22) Filed: Jun. 5, 2019

(65) Prior Publication Data

US 2019/0345038 A1 Nov. 14, 2019

Related U.S. Application Data

(63) Continuation of application No. 16/094,784, filed as application No. PCT/EP2017/076325 on Oct. 16, 2017, now Pat. No. 10,351,437.

(30) Foreign Application Priority Data

Oct. 17, 2016 (EP) .................................... 16194209

(51) Int. Cl.
*C01F 11/46* (2006.01)
*A61K 8/19* (2006.01)
(Continued)

(52) U.S. Cl.
CPC .............. *C01F 11/466* (2013.01); *A61K 8/19* (2013.01); *A61K 47/02* (2013.01); *A61Q 19/00* (2013.01);
(Continued)

(58) Field of Classification Search
CPC ........ C01F 11/46; C01F 11/466; A61K 9/143; A61K 9/16; A61K 9/2004; A61K 9/2009;
(Continued)

(56) References Cited

U.S. PATENT DOCUMENTS

| 3,956,456 A | 5/1976 | Keller et al. |
| 6,030,636 A | 2/2000 | Randolph et al. |

(Continued)

FOREIGN PATENT DOCUMENTS

| DE | 3141746 A1 | 5/1983 |
| DE | 19620117 C1 | 7/1997 |

(Continued)

OTHER PUBLICATIONS

Christensen, A. N., et al., "Formation and Transformation of Five Different Phases in the $CaSO_4$—$H_2O$ System: Crystal Structure of the Subhydrate $\beta$-$CaSO_4 \cdot 0.5H_2O$ and Soluble Anhydrite $CaSO_4$," *Chem. Mater.* 20(6): 2124-2132, The American Chemical Society, United States (2008).

(Continued)

*Primary Examiner* — Timothy C Vanoy
(74) *Attorney, Agent, or Firm* — Sterne, Kessler, Goldstein & Fox P.L.L.C.

(57) ABSTRACT

The present invention relates to a new method for producing a calcium sulphate hemihydrate with unique properties for use for therapeutic applications in the cosmetic or pharmaceutical industry. Calcium sulphate hemihydrate is a biocompatible and biodegradable inorganic substance and thus suitable as a carrier in pharmaceutical compositions, e.g. a controlled release composition, containing at least one pharmaceutically active ingredient.

20 Claims, 1 Drawing Sheet

Drug release over time of four test lumps that passed the disintegration test.

(51) Int. Cl.
*A61K 47/02* (2006.01)
*A61Q 19/00* (2006.01)
*A61Q 19/08* (2006.01)
*A61K 9/16* (2006.01)

(52) U.S. Cl.
CPC .......... *A61Q 19/08* (2013.01); *A61K 9/1611* (2013.01); *A61K 2800/10* (2013.01)

(58) Field of Classification Search
CPC ...... A61K 9/2077; A61K 9/485; A61K 47/00; A61K 47/02
See application file for complete search history.

(56) References Cited

U.S. PATENT DOCUMENTS

| | | | |
|---|---|---|---|
| 6,437,000 | B1 | 8/2002 | Mulye |
| 9,895,354 | B2 | 2/2018 | Puleo et al. |
| 10,351,437 | B2 * | 7/2019 | Axen ..................... A61Q 19/00 |
| 2012/0203356 | A1 | 8/2012 | Mamidwar et al. |
| 2015/0086647 | A1 | 3/2015 | Lakaye et al. |

FOREIGN PATENT DOCUMENTS

| | | |
|---|---|---|
| GB | 2 205 089 A | 11/1988 |
| WO | WO 2007/104549 A2 | 9/2007 |
| WO | WO 2013/152418 A1 | 10/2013 |

OTHER PUBLICATIONS

Christensen, A. N., et al., "A new calcium sulfate hemi-hydrate," *Dalton Trans.* 39(8): 2044-2048, The Royal Society of Chemistry, United Kingdom (2010).

Wang, P., et al., "Calcium Sulfate Hemihydrate Powders with a Controlled Morphology for Use as Bone Cement." *J. Am. Ceram. Soc.* 91(6): 2039-2042, The American Ceramic Society, United States (2008).

Written Opinion and International Search Report for International Application No. PCT/EP2017/076325, European Patent Office, Munich, dated Jan. 17, 2018 (8 pages).

Hesaraki, S., et al., "Evaluation of a bioceramic-based nanocomposite material for controlled delivery of a non-steroidal anti-inflammatory drug," *Medical Engineering & Physics* 31(10):1205-1213, Elsevier Ltd., United Kingdom (2009).

Lin, M., et al., "Novel highly bioactive and biodegradable gypsum/calcium silicate composite bone cements: from physicochemical characteristics to in vivo aspects," *Journal of Materials Chemistry B* 2(14): 2030-2038, The Royal Society of Chemistry, United Kingdom (2014).

European Search Report mailed for EP Appl. No. 19155080.5 dated Apr. 25, 2019, European Patent Office, Munich, Germany (10 pages).

An English language partial machine translation of DE 3141746 A1 (cited as document FP3) from Espacenet, Patent Translate, Powered by EPO and Google, May 31, 2019 (7 pages).

Notice of Allowance dated Mar. 4, 2019, in U.S. Appl. No. 16/094,784, Axén et al., having a 371(c) date of Oct. 18, 2018.

* cited by examiner

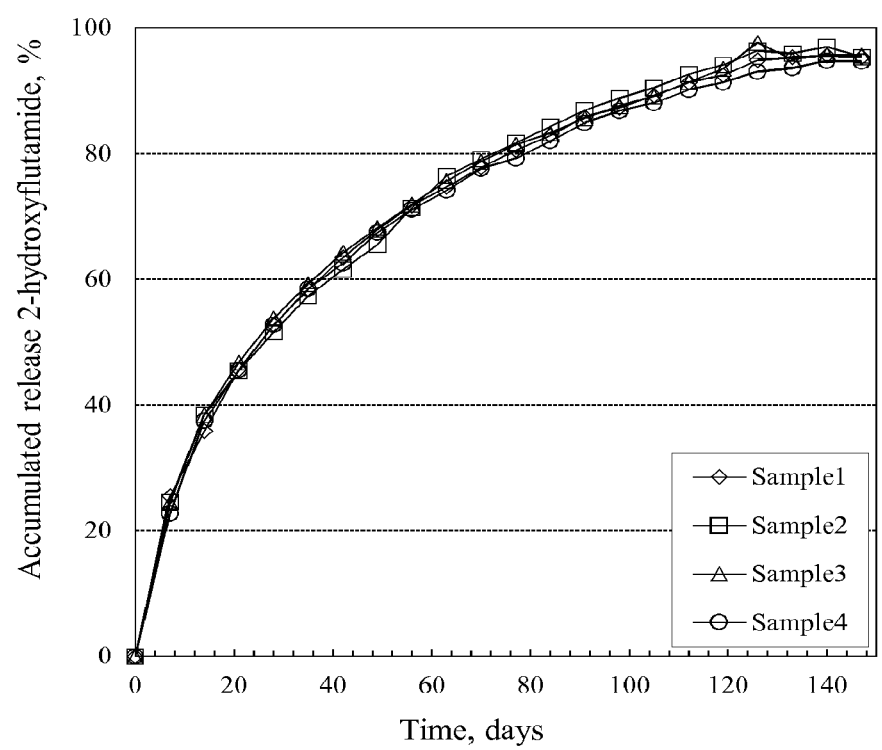
Drug release over time of four test lumps that passed the disintegration test.

ofMETHOD FOR PRODUCING CALCIUM SULPHATE HEMIHYDRATE WITH UNIQUE PROPERTIES

FIELD OF THE INVENTION

The present invention relates to a new method for producing a calcium sulphate hemihydrate for use in the cosmetic, therapeutic or pharmaceutical industries. Calcium sulphate hemihydrate is a biocompatible and biodegradable inorganic substance and thus suitable as a carrier in pharmaceutical compositions, e.g. a controlled release composition, containing at least one pharmaceutically active ingredient. Calcium sulphate may also be used alone as a filler tissue material for either cosmetic or therapeutic applications.

BACKGROUND

The present invention relates to a process of producing inorganic compositions suitable as carriers for pharmaceutically active compounds to be administered to human beings or to any other mammal.

Calcium sulphate is used for a variety of purposes and exists in various forms and states of hydration.

The calcium sulphate hydrates, in particular gypsum (calcium sulphate dihydrate) and the hemi-hydrate, are used in a number of industrial applications for a wide range of purposes, e.g. as an additive for the production of cements, gypsum wallboards, or bone void fillers for orthopaedic and dental applications. Some of these void filler products also contain an active pharmaceutical ingredients whereby a slow release pharmaceutical composition is achieved. In the form of γ-anhydrite (the anhydrous form), calcium sulphate is used as a desiccant.

Calcium sulphate hemihydrate exists in at least two distinct morphological forms, denoted α and β. The preparation route is of crucial importance for which of the two forms that is obtained. Christensen et al in Dalton Trans., 2010, 39, 2044-2048 suggests that the α-form can be obtained at hydrothermal conditions, i.e. temperature range of 120 to 160° C. and at pressures up to 8 bar, while the β-form can be obtained by dry heating in the temperature range 120 to 180° C. At temperatures above 170° C. γ-anhydrite may begin to form, Christensen et al, Chem. Mater. 2008, 20, 2124-2132.

It has been found that the method of manufacturing the calcium sulphate hemihydrate is essential for the dissolution characteristics of a formulation prepared by the hemihydrate, i.e. relevant for the drug release rate into a patient. This is surprisingly the case even if the calcium sulphate hemihydrate has re-crystallized into calcium sulphate dihydrate during the process for preparing the pharmaceutical composition. It is thus important to be able to control the product characteristics of a method for preparing calcium sulphate hemihydrate.

The present invention relates to a process of producing inorganic compositions suitable as carriers for therapeutically active substances to be administered to the human body or any other mammals. The compositions of the invention are based on calcium sulphate and are applicable for several drug delivery purposes; for example, for targeted treatment of specific parts of the body such as diseased organs or for localised treatment of e.g. cancer such as prostate cancer e.g. through targeted and local release of hormonal and anti-hormonal agents.

DETAILED DESCRIPTION OF THE INVENTION

It has been found that, calcium sulphate hemihydrate prepared according to the present invention can advantageously be used to prepare pharmaceutical compositions with reproducible and good dissolution characteristics. Such pharmaceutical compositions give a controllable drug release rate into serum or body tissue of a patient.

BRIEF DESCRIPTION OF THE DRAWING

FIG. 1 shows drug release over time of four test lumps that passed the disintegration test.

One aspect of the present invention is a method for producing calcium sulphate hemihydrate powder comprising the steps of:
a. treating calcium sulphate dihydrate in a closed cabinet with controlled temperature, air circulation in the cabinet and a controlled air outflow from the cabinet;
b. adjusting the temperature to above 100° C.;
c. allowing for a process time of 1-12 hours; and
d. adjusting the moist air outflow from the cabinet to 0.2-2 L/s.

In one aspect of the present invention the temperature in method step b is about 150-220° C.

In one aspect of the present invention the temperature in method step b is about 180-210° C.

In one aspect of the present invention the temperature in method step b is about 185-205° C.

In one aspect of the present invention the temperature in method step b is about 190-203° C.

In one aspect of the present invention the temperature in method step b is about 200° C.

In one aspect of the present invention the time in method step c is 2-8 hours.

In one aspect of the present invention the time in method step c is 3-5 hours.

In one aspect of the present invention the time in method step c is 3.5-4.5 hours.

In one aspect of the present invention the time in method step c is about 4 hours.

In one aspect of the present invention the moist air outflow in method step d is 0.2-1.5 L/s.

In one aspect of the present invention the moist air outflow in method step d is 0.25-1 L/s.

In one aspect of the present invention the moist air outflow in method step d is 0.25 Us and 0.8 L/s.

In one aspect of the present invention the moist air outflow in method step d is 0.3 L/s and 0.7 L/s.

In one aspect of the present invention the moist air outflow in method step d is 0.4 L/s and 0.6 L/s.

In one aspect of the present invention the moist air outflow in method step d is about 0.5 L/s.

Suitable process temperatures for the method of the present invention are above 100° C., such as 150, 160, 170, 180, 185, 190, 195, 200, 203, 205, 210, 215 or 220° C.

Suitable process times for the method of the present invention are 1, 2, 3, 3.5, 4, 4.5, 5, 6, 7, 8, 9, 10, 11 or 12 hours.

Suitable moist air outflows through the outlet for the method of the present invention are 0.2, 0.25, 0.3, 0.35, 0.4, 0.45, 0.5, 0.55, 0.6, 0.7, 0.8, 0.9, 1, 1.5, or 2 L/s.

The starting material, calcium sulphate dihydrate, is commercially available from several suppliers. The total water or moisture content varies between suppliers and batches. Total water or moisture content of pharmaceutical products, like calcium sulphate, can include both bound water (water of hydration) where water is a part of the crystal structure and free water. Calcium sulphate dihydrate, contains 2 water molecules of bound water (water of hydration) per molecule of calcium sulphate and about X weight-% of free water. Total moisture content can be determinate by various techniques like gravimetric method or Karl Fisher Titration. The distinction and accurate measurement of bound versus free water is thermal gravimetric analysis (TGA) where weight loss as a function of temperature allows estimation of water content in percentage.

In another aspect of the present invention the calcium sulphate dihydrate is loaded stepwise into the closed cabinet in order to control and maintain the temperature at a correct level and avoiding sudden drop in temperature.

Conventional pharmaceutical equipment for heating and/or drying processes of powders can be described with the amount of complete cabinet air volume exchanges per hour. For a smaller heating cabinet of approximately 100-150 dm$^3$, a volume exchange may be 20/hour and for a larger heating cabinet of approximately 350-600 dm$^3$ the volume exchange may be 60/hour. The volume exchange and cabinet volume correlates approximately linearly. What has been found with the present invention is that the outflow air needs to be in the range of 0.2-2 L/s irrespective of the cabinet volume in order to have a constant intermediately humid milieu in the cabinet and loading up to about 1.5 kg which corresponds to about 20 g free moist or water. The volume exchanges expressed as cabinet volumes per hour corresponding to an air outflow of 0.5 L/s are 12-18 for the smaller cabinet and 3-5 for the larger cabinet.

The amount of powder loaded at the same time into the cabinet should be in the range of 0.01 to 20 kg/m$^3$, preferably about 0.05 to 5 kg/m$^3$.

The present invention relates to a new method for producing a calcium sulphate hemihydrate of high chemical purity, and of high morphological purity. The method of the present invention provides calcium sulphate hemihydrate, substantially in the β-form but with some degree of amorphous content.

In one aspect, the present invention relates to injectable in vivo solidifying modified-release pharmaceutical compositions comprising drug substance/s and drug carriers manufactured from calcium sulphate. The compositions are administered through a needle in a fluid state and are designed to solidify at the site of injection and to deliver the drug substance/s to specific regions where their pharmacological effects are desired. For example, the composition is suitable for use in the treatment of localized cancer. The method for preparing the solidifying material is unique and unconventional both regarding parameter settings in the pharmaceutical industry and regarding what is currently described for the material behaviour in the field of materials science.

An in vivo solidifying formulation of calcium sulphate is at least partly composed of calcium sulphate hemihydrates. The hemihydrates are produced from calcium sulphate dihydrate by a heat treatment. It has been found that the details of the heat treatment procedure are essential for the properties of the formulation.

Uses

Calcium sulphate hemihydrate prepared according to the present invention can be used as a carrier for pharmaceutically active ingredients in a pharmaceutical composition to be administered to human beings or any other mammal. The release rate of the pharmaceutically active ingredient may is influenced by the way the pharmaceutical composition is prepared. It is thus possible to prepare pharmaceutical compositions, comprising calcium sulphate hemihydrate prepared according to the present invention, for immediate, delayed and controlled release or a combination thereof.

Calcium sulphate hemihydrate, prepared according to the present invention, can further be used as a starting material for preparing other forms of calcium sulphate, such as calcium sulphate dihydrate. Calcium sulphate hemihydrate prepared according to the present invention will influence the physical properties of such calcium sulphate dihydrate.

Loading of the Active Pharmaceutical Ingredient (API)

Calcium sulphate hemihydrate prepared according to the present invention can be conventionally milled to achieve the right particle size distribution of the powder.

The active pharmaceutical ingredient (API) may be loaded onto the calcium sulphate hemihydrate, prepared according to the present invention, in different ways. The calcium sulphate hemihydrate can for example be mixed with the API creating an API-loaded binary mixture. This may be performed by dry mixing. This may also be performed by dissolving the API in a solvent to which the calcium sulphate is inert (such as an alcohol). This leads to a slurry of calcium sulphate powder in a solute of API and solvent. By evaporating the solvent while agitating the slurry a dry powder of API and calcium sulphate is formed.

The loading of the API can further be done simultaneously as the calcium sulphate hemihydrate, prepared according to the present invention, is converted into other forms of calcium sulphate, such as recrystallized into calcium sulphate dihydrate. The API-loaded calcium sulphate dihydrates in such a formulation will have different physical properties and release rates/release profiles depending on how the precursor calcium sulphate hemihydrate was prepared.

Such binary mixture can further be conventionally compressed in API-loaded dense granules (or bodies). The API-loaded dense granules (or bodies) will have different physical properties and release rates/release profiles depending on how it is prepared, for example which pressure that was used in the densifying step. Suitable pressures are 1000-5000 bar for about 1-3 hours.

Preferably, such API-loaded dense granules (or bodies) are prepared by wetting calcium sulphate hemihydrate, prepared according to the present invention, with enough water to convert it to calcium sulphate dihydrate and simultaneously apply a pressure of about 4000 bar for about 1 hour.

An isostatic press is a suitable apparatus for applying pressures up to 5000 bar.

A method for producing such dense granules is described in WO2007/104549.

It is known from technical applications, that calcium sulphate hemihydrate which is mixed with water and left to solidify, and which thereby forms calcium sulphate dihydrate, forms solidified materials of different characteristics, primarily carrying mechanical strengths, depending on the characteristics of the starting powder (e.g. alfa or beta hemi-hydrate).

The calcium sulphate hemihydrate prepared according to present invention can be further processed for example by conventional milling into a suitable average particle size distribution.

A pharmaceutical composition containing the calcium sulphate prepared according to the present invention may contain at least one additional pharmaceutically active ingredient.

The pharmaceutical composition (drug product), prepared using calcium sulphate hemihydrate prepared according to the present invention, is applicable with any therapeutically, prophylactically and/or diagnostically active substances that may require a controlled release, especially a prolonged controlled release. Examples of relevant pharmacological classes are e.g. anti-cancer agents. With regard to anticancer agents, i.e. neoplastic agents, the invention may be used for targeted and controlled local release of hormonal, anti-hormonal, chemotherapeutic and/or other pharmacological agent(s). It may also be used in therapeutic applications without adding an active substance such as a bone filler or as a cosmetic application such as for wrinkles and/or plastic surgery.

Of particular interest are drug products containing calcium sulphate hemihydrate, prepared according to the present invention, for use in the treatment of prostate diseases, more specifically benign prostatic hyperplasia, prostate cancer and/or prostatite. For the treatment of prostate related diseases is may be especially useful to use anti-cancer agents such specific anti-androgens. More preferably, the one or more therapeutically, prophylactically and/or diagnostically active substances are flutamide, hydroxyflutamide, cyproteron, nilutamide or bicalutamide or the like.

Additionally, in some cases it may be favourable to use a combination of an anti-androgen and a gonadotropin-releasing hormone or an analogue thereof. Preferably, the one or more therapeutically, prophylactically and/or diagnostically active substances in a highly densified calcium sulphate, prepared according to the present invention, are suitable for use in prostate related diseases or conditions. Furthermore, the active substance is an androgen or a derivative thereof, an anti-androgen or a derivative thereof, an oestrogen or a derivative thereof, an anti-oestrogen or a derivative thereof, a gestagen or a derivative thereof, an anti-gestagen or a derivative thereof, an oligonucleotide, a progestagen or a derivative thereof, a gonadotropin-releasing hormone or an analogue or derivative thereof, a gonadotropin inhibitor or a derivative thereof, an adrenal and/or prostate enzyme inhibitor, a membrane efflux and/or membrane transport protein, an immune system modulator, an angiogenesis inhibitor, or combinations thereof.

A drug product containing calcium sulphate hemihydrate, prepared according to the present invention, may also include any other suitable active substance suitable for application in soft tissues or organs for local or systemic sustained drug release. Such drug product can also be explored in other treatments e.g.: pain, neurological diseases (Alzheimer, Parkinson), autoimmune diseases, immunological diseases, and diseases responding to immunological and immunomodulating therapy (hepatitis, MS, tumours), infections, inflammations, metabolic diseases, obesitas, diseases in the uro-genital tract, cardiovascular diseases (including blood pressure), hematopoietic, anticoagulant, thrombolytic and antiplatelet diseases, chemotherapy of parasitic infections, microbial diseases and neoplastic diseases, hypercholesterolemia, dyslipidemia, hematopoetic diseases, respiratory diseases (asthma, chronical lung obstruction), diseases of the kidney, gastrointestinal diseases, liver diseases, hormonal disruption, replacement and substitution, vitamins replacement and substitution.

Examples of active substances from various pharmacological classes for the use in drug products containing calcium sulphate hemihydrate, prepared according to the present invention, can be used include e.g. antibacterial agents, antihistamines and decongestants, anti-inflammatory agents, antiparasitics, antivirals, local anaesthetics, antifungals, amoebicidals or trichomonocidal agents, analgesics, antianxiety agents, anticlotting agents, antiarthritics, antiasthmatics, anticoagulants, anticonvulsants, antidepressants, antidiabetics, antiglaucoma agents, antimalarials, antimicrobials, antineoplastics, antiobesity agents, antipsychotics, antihypertensives, auto-immune disorder agents, anti-impotence agents, anti-Parkinsonism agents, anti-Alzheimers agents, antipyretics, anticholinergics, anti-ulcer agents, anorexics, beta-blockers, beta-2 agonists, alpha receptor antagonists and agonists, blood glucose-lowering agents, bronchodilators, agents with effect on the central nervous system, cardiovascular agents, cognitive enhancers, contraceptives, cholesterol-reducing agents, agents against dyslipidemia, cytostatics, diuretics, germicidals, H-2 blockers, hormonal agents, anti-hormonal agents, hypnotic agents, inotropics, muscle relaxants, muscle contractants, physic energizers, sedatives, sympathomimetics, vasodilators, vasoconstrictors, tranquilizers, electrolyte supplements, vitamins, uricosurics, cardiac glycosides, membrane efflux inhibitors, membrane transport protein inhibitors, expectorants, purgatives, contrast materials, radiopharmaceuticals, imaging agents, peptides, enzymes, growth factors, vaccines, mineral trace elements, etc.

The therapeutically, prophylactically and/or diagnostically active drug substance(s) may also be in the form of a pharmaceutically acceptable salt, solvate or complex thereof or in any suitable crystalline or amorphous form or in the form of a pro-drug.

In a specific embodiment the active substance is one or more cytostatics such as one or more alkylating agents, one or more antimetabolites, one or more antimitotics, one or more topoisomerase inhibitors, one or more biological cytoregulators, one or more hormone or antihormones and the like.

More specifically, the one or more active substance may be an alkylating agent like e.g. mephalan, busulfan, carboplatin, cisplatin, cyclophosphamid, dacarbazin, chlorambucil, lomustin, carboplatin, temozolomid, treosulfan; an antimetabolite like e.g. pemetrexed, cytarabin, azathioprin, fludarabinphosphat, fluoruracil, hydroxyurea, cladribin, methotrexat, tegafur, uracil, capecitabin;

an antimicotics like e.g. vinorelbin, vinkristin, pacitaxel, docetaxel, vinblastin;

a topoisomerase inhibitor like e.g. doxorubicin, amsakrin, irinotecan, daunorubicin, epirubicin, etoposid, idarubicin, topotecan, mitomycin, mitoxantron;

a biological cytoregulator like e.g. bleomycin;

a hormone or antihormone like e.g. polyestradiolphosphate, estradiol, anastrozol, exemestan, fluvestrant, letrozol, tamoxifen, megestrolacetate, medroxyprogesteron acetate, octreotid, triptorelin, leuprorelin, buserelin, goserelin;

asparaginase, tyrosinkinase inhibitor like e.g. imatinib other agents like e.g. mitotan, celecoxib, lenograstim, interferon γ-1b interferon α-2b, pegfilgrastim, filgrastim, aldesleukin, bevacizumab, cetuximab, trastuzumab, alemtuzumab, rituximab, bortezomib, temoporfin, methylaminolevulinat, anagrelid, estramustinphosphat.

In a preferred aspect, the active substance is suitable for the treatment of prostate related diseases or conditions.

Drug products containing calcium sulphate hemihydrate, prepared according to the present invention, can be applied locally with minimally invasive techniques, and a sustained (controlled) local release profile of the drug over a prolonged period of time can be obtained. Such local and sustained delivery of active substances optimises the local concentration-time profile of the active substances and their local pharmacological effects, and minimises the systemic exposure and thus reduces the side-effects, and hence increases the safety and utility of the active substance and the pharmaceutical composition containing the active substance. In addition the compliance of the therapy is enhanced.

Other preferred drug products containing calcium sulphate hemihydrate, prepared according to the present invention, are those wherein the therapeutically, prophylactically and/or diagnostically active substance is an androgen or a derivative thereof, an anti-androgen or a derivative thereof, an oestrogen or a derivative thereof, an anti-oestrogen or a derivative thereof, a gestagen or a derivative thereof, an anti-gestagen or a derivative thereof, an oligonucleotide, a progestagen or a derivative thereof, a gonadotropin-releasing hormone or an analogue or derivative thereof, a gonadotropin inhibitor or a derivative thereof, an adrenal and/or prostate enzyme inhibitor, a membrane efflux and/or membrane transport protein, an immune system modulator, an angiogenesis inhibitor, or combinations thereof.

Disintegration Test

The disintegration test was performed by placing three moulded lumps of a solidified test formulation A-G, each weighing about 300 mg, diametrically opposite and near the edge on the bottom of a glass crystallizing dish of 190 mm diameter containing 1 L of a 0.9% NaCl aqueous solution.

0.59 g of API-loaded matrix; and C) 0.59 g of API-loaded granules in a syringe together with 1.6 mL 0.25% Na-CMC aqueous solution. The syringe content was well mixed so that the mixture forms a paste from which three samples, weighing about 300 mg each, were ejected onto an inert surface and solidified within 30 minutes to what is referred to as moulded lumps, with circular shape and a flat bottom.

Unloaded matrices were prepared by conventional milling of calcium sulphate hemihydrate, prepared according to the present invention, to an average particle size of 2 μm.

API-loaded matrices were prepared from the unloaded matrix. The unloaded matrix (75 g) was suspended in a solution, of the drug substance 2-hydroxyflutamide (75 g) in isopropanol. The suspension was allowed to dry under stirring to create API-loaded matrices, consisting of calcium sulphate hemihydrate, prepared according to the present invention, and the drug substance 2-hydroxyflutamide.

API-loaded granules were prepared from the API-loaded matrices. The API-loaded matrices (150 g) were wetted with water (15 mL) and placed in an isostatic press for 1 hour at a pressure of 4000 bar, whereby the calcium sulphate hemihydrate, prepared according to the present invention, in the API-loaded matrixes recrystallizes into calcium sulphate dihydrate, and forms dense structure of calcium sulphate dihydrate encapsulating the API. This creates API-loaded granules consisting of calcium sulphate dihydrate and entrapped drug substance 2-hydroxyflutamide. The API-loaded granules are thereafter, crushed, milled and sieved into a particle size of 125-300 μm to be used in the disintegration test.

TABLE 1

Disintegration test

| Example | Loading amount $Ca_2SO_4 \cdot 2H_2O$ | Loading container | Temp | Time | Air outflow (L/s) | Disintegration test |
|---------|---------------------------------------|-------------------|------|------|-------------------|---------------------|
| A | 6 × 500 g Stepwise loading 1000 g × 3 | Crystallization dish | 200° C. | 4 h | >10 | Fail |
| B | 2 × 250 g | Crystallization dish | 200° C. | 4 h | 2 | Fail |
| C | 2 × 250 g | Crystallization dish | 200° C. | 4 h | 0 | Fail |
| D | 6 × 500 g Stepwise loading 1000 g × 3 | Crystallization dish | 200° C. | 4 h | 2 | Fail |
| E | 12 × 500 g Stepwise loading 1000 g × 6 | Crystallization dish | 200° C. | 4 h | 2 | Fail |
| F | 6 × 500 g Stepwise loading 1000 g × 3 | Crystallization dish | 200° C. | 4 h | 2 | Fail |
| G | 16 × 500 g Stepwise loading 1000 g × 8 | Crystallization dish | 200° C. | 4 h | 0.5 | Pass |
| H | 16 × 500 g Stepwise loading 1000 g × 8 | Crystallization dish | 200° C. | 4 h | 0.2 | Pass (borderline) |
| I | 16 × 500 g Stepwise loading 1000 g × 8 | Crystallization dish | 200° C. | 4 h | 0.8 | Pass |

The lumps were visually evaluated after 24 hours and thereafter daily. The test formulations A-G were marked as pass in Table 1, if the lumps had maintained their original shape after 48 hours, but marked as failed in Table 1 if the lumps had started to disintegrate and thereby lost their original shape after 48 hours.

Each test formulation A-G were prepared by suspending a mixed powder consisting of A) 0.45 g unloaded matrix; B)

Drug release over time of four test lumps from the same formulation batch containing the active agent 2-hydroxyflutamide that passed the disintegration test is shown below in FIG. 1.

It has been shown that a continuous and smooth release curve requires the moulded lumps to dissolve slowly/gradually without decomposition (falling apart/disintegration). If the moulded lump falls apart/disintegrates then the drug release increases strongly. The disintegration test described above is thus a fast way to check the quality of test formulations A-G without analyzing the drug release.

It is thus essential for a slow and continuous drug release that the formulation forms well cohesive lumps. It has been found that the cohesiveness of the molded lumps is depending on how the calcium sulphate hemihydrates are prepared. Molded lumps prepared from calcium sulphate hemihydrates prepared according to the present invention all passed the disintegration test described above.

The present invention also relates to calcium sulphate hemihydrate powder obtainable by any of the processes described herein.

EXAMPLES

General Procedure

Typically, the calcium sulphate hemihydrate is prepared as follows: Calcium sulphate dihydrate from Carl Roth (article No. 0256.3) is poured into cylindrical glass crystallization dishes with a diameter of 190 mm. 500 g of free flowing powder is distributed evenly in each glass crystallization dish, which generally corresponds to a powder bed thickness of approximately 30-40 mm. An adequate number of crystallization dishes is inserted into the pre-heated heating cabinet at 200° C. with an air outflow of about 0.5 L/s. After four hours heating, the hemihydrate has been produced and is taken out of the cabinet to cool down at room temperature for at least 30 minutes. A representative sample may be removed for further processing and evaluation in the disintegration test.

Test formulations A-G were prepared using the general procedure above and representative samples were removed and evaluated in the disintegration test. Results from the disintegration test is given in Table 1.

The invention claimed is:

1. Calcium sulphate hemihydrate powder obtainable by a method comprising the steps of
   a. treating calcium sulphate dihydrate in a closed cabinet with controlled temperature, air circulation in the cabinet and an adjustable air outflow from the cabinet;
   b. adjusting the temperature to from above 100 to 220° C.;
   c. allowing for a process time of 1-12 hours; and
   d. adjusting the moist air outflow from the cabinet to 0.2-1.5 L/s.

2. The calcium sulphate hemihydrate powder according to claim 1, wherein the calcium sulphate hemihydrate is substantially in the β-form.

3. The calcium sulphate hemihydrate powder according to claim 1, wherein the powder is milled to achieve a desirable particle size.

4. The calcium sulphate hemihydrate powder according to claim 3, wherein the powder is milled to an average particle size of 2 μm.

5. A pharmaceutical composition, comprising a calcium sulphate hemihydrate powder according to claim 1.

6. The pharmaceutical composition according to claim 5, which is an injectable in vivo solidifying composition.

7. The pharmaceutical composition according to claim 5, wherein the composition is compressed into dense bodies.

8. The pharmaceutical composition according to claim 5, further comprising at least one pharmaceutically active ingredient.

9. The pharmaceutical composition according to claim 8, wherein the at least one pharmaceutically active ingredient is selected from antineoplastic agents, antibacterial agents, antihistamines, anti-inflammatory agents, alkylating agents, antimitotics, topoisomerase inhibitors, biological cytoregulators, hormones, anti-hormones and vaccines.

10. The pharmaceutical composition according to claim 8, wherein said calcium sulphate hemihydrate powder is a carrier for the at least one pharmaceutically active ingredient.

11. The pharmaceutical composition according to claim 10, wherein the calcium sulphate hemihydrate powder carrier is adapted for immediate, delayed, controlled or sustained release, or any combination thereof, of the at least one pharmaceutically active ingredient.

12. A method of preparing a pharmaceutical composition, comprising loading at least one pharmaceutically active ingredient onto calcium sulphate hemihydrate powder obtained by a method comprising the steps of
   a. treating calcium sulphate dihydrate in a closed cabinet with controlled temperature, air circulation in the cabinet and an adjustable air outflow from the cabinet;
   b. adjusting the temperature to from above 100 to 220° C.;
   c. allowing for a process time of 1-12 hours; and
   d. adjusting the moist air outflow from the cabinet to 0.2-1.5 L/s.

13. The method according to claim 12, wherein said loading comprises mixing the powder with the at least one pharmaceutically active ingredient.

14. The method according to claim 12, wherein the calcium sulphate hemihydrate is substantially in the β-form.

15. The method according to claim 14, wherein the powder is milled to a desirable particle size.

16. The method according to claim 15, wherein the powder has an average particle size of 2 μm.

17. The method according to claim 12, wherein the composition is an injectable in vivo solidifying composition.

18. The method according to claim 12, wherein the composition is compressed into dense bodies.

19. The method according to claim 12, wherein the at least one pharmaceutically active ingredient is selected from antineoplastic agents, antibacterial agents, antihistamines, anti-inflammatory agents, alkylating agents, antimitotics, topoisomerase inhibitors, biological cytoregulators, hormones, anti-hormones and vaccines.

20. The method according to claim 12, wherein the composition is adapted for immediate, delayed, controlled or sustained release, or any combination thereof, of the at least one pharmaceutically active ingredient.

* * * * *